United States Patent [19]

Gorvin

[11] 4,337,274

[45] Jun. 29, 1982

[54] FLUKICIDAL COMPOUNDS

[75] Inventor: John H. Gorvin, London, England

[73] Assignee: Burroughs Wellcome Co., Research Triangle Park, N.C.

[21] Appl. No.: 43,492

[22] Filed: May 29, 1979

[30] Foreign Application Priority Data

May 30, 1978 [GB] United Kingdom ............... 24035/78

[51] Int. Cl.³ ............................................. A61K 31/18
[52] U.S. Cl. .................................... 424/321; 424/320; 424/324; 564/86; 564/101; 564/102
[58] Field of Search ........................ 260/562 P, 551 S; 424/321, 324, 320; 564/86, 101, 102

[56] References Cited

U.S. PATENT DOCUMENTS

| 2,969,350 | 1/1961 | Dorlars et al. | 260/148 |
|---|---|---|---|
| 3,223,582 | 12/1965 | Bindler et al. | 260/562 P |
| 3,423,470 | 1/1969 | Rohr et al. | 260/556 B X |
| 3,798,258 | 3/1974 | Patchett et al. | 424/324 |
| 3,829,487 | 8/1974 | Mrozik | 424/321 |
| 3,840,597 | 10/1974 | Moore et al. | 260/562 P |
| 3,965,113 | 6/1976 | Beard et al. | 548/306 |
| 3,976,784 | 8/1976 | Coles et al. | 424/324 |
| 4,034,110 | 7/1977 | Mitrovic et al. | 424/321 |
| 4,082,851 | 4/1978 | Feit et al. | 424/300 |
| 4,198,407 | 4/1980 | Rösner et al. | 424/249 |

FOREIGN PATENT DOCUMENTS

| 2921824 | 6/1979 | Fed. Rep. of Germany | 424/321 |
|---|---|---|---|
| 773032 | 11/1934 | France | 564/86 |
| 2008065 | 7/1969 | France . | |
| 2212149 | 7/1974 | France . | |
| 2391203 | 12/1978 | France . | |

OTHER PUBLICATIONS

Chem. Abstracts 51:6539–51:6540.

Primary Examiner—Ethel G. Love
Attorney, Agent, or Firm—Donald Brown

[57] ABSTRACT

Diphenylethers of the formula:

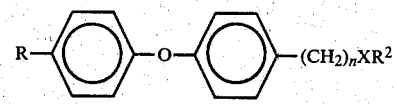

their synthesis, formulations containing them, methods of making such formulations, and their use in the treatment of liver fluke infections in mammals.

17 Claims, No Drawings

FLUKICIDAL COMPOUNDS

This invention relates to novel compounds, their preparation, formulations containing them, methods of making such formulations and to their use in the treatment of liver fluke infections in mammals.

Animals are infected with liver fluke when eating forage contaminated with encysted forms of cercariae, an intermediate stage in the life cycle of the fluke. The cercariae emerge from the cysts in the intestine of the host animal, penetrate the intestine wall, and make their way to the liver. At this stage they are microscopic in size, but grow as they wander around the liver parenchyma. This causes considerable destruction of the liver tissue and can give rise to the syndrome of acute fascioliasis which normally leads to the death of the host when massive infections are present. If the animal survives, the flukes eventually reach the bile ducts where they mature into adult worms. The presence of a massive infection in the bile ducts gives rise to the syndrome of chronic fascioliasis which is a serious debilitating disease of the host animal. In the past most liver fluke remedies have been known to kill only the adult and semiadult worms, and the immature worms have been resistant to attack by such remedies. However the compounds disclosed in U.K. Pat. No. 1,380,882 are effective in combatting infections of liver flukes in mammals, and are especially active in combatting infections of immature worms of Fasciola spp.

It has now been found by the Applicants that the novel compounds of formula (I) are effective in combatting infections of liver flukes in mammals.

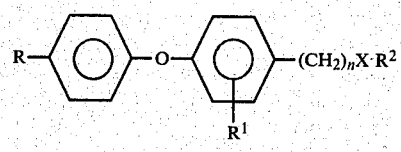

In formula (I):
R is selected from amino, monoalkanoylamino and dialkanoylamino, both of one to four carbon atoms;
$R^1$ is selected from hydrogen, alkyl of one to four carbon atoms, alkenyl of two to five carbon atoms and halo;
$R^2$ is $NR^8R^9$ wherein $R^8$ is selected from alkyl of one to four carbon atoms, hydroxyalkyl of one to four carbon atoms, aryl of six of ten carbon atoms and cycloalkyl of three to eight carbon atoms, and
$R^9$ is selected from $R^8$ as defined and hydrogen;
X is S, SO or $SO_2$; and
n is 0, 1, 2 or 3.

As a subclass of the compounds of formula (I) may be mentioned those compounds of formula (I) wherein $R^8$ or $R^9$ is phenyl.

It will be appreciated by persons skilled in the art that acid addition salts may be formed of the compounds of formula (I). Unless the context indicates otherwise, wherever in the following reference is made to 'compounds of formula (I)' it should be understood that this term includes the acid addition salts of the compounds.

The compounds of formula (I) may be prepared by standard methods well known in the art for the synthesis of compounds of analogous structure. Particular routes of synthesis which may be employed are dependent upon the chemical structure of the compound in question and will vary according to the reactive functional groups present in each compound.

The preparation of compounds of formula (I) wherein R is amino includes the reduction of a compound of formula (II):

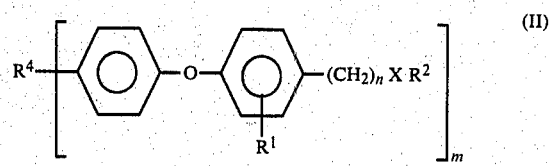

wherein $R^1$, $R^2$, n, and X are as defined previously, m is 1 or 2 and when m is 1, $R^4$ is nitro or nitroso; and when m is 2, $R^4$ is azo or azoxy.

The reduction may be conveniently effected by standard methods well-known in the art which include reaction with hydrogen in the presence of a metal or other hydrogen catalyst and a solvent such as aqueous acid, ethanol, or acetic acid; a metal and aqueous acid, for example, iron powder and dilute aqueous or ethanolic hydrochloric acid; and reducing agents such as stannous chloride in concentrated hydrochloric acid, ferrous hydroxide suspended in aqueous or ethanolic ammonia, iron powder in glacial acetic acid, aqueous dithionite or other reagents known in the art to reduce nitro and nitroso compounds to amines.

Such reduction can be run in the presence of acylating agents (as described hereinbelow) to produce compounds of formula (I) wherein R is mono- or dialkanoylamino without isolation of the corresponding amine.

The preparation of compounds of formula (II) wherein $R^4$ is nitroso includes the reaction of a compound of formula (III):

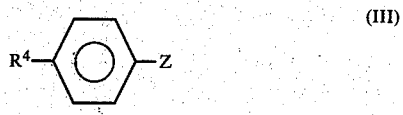

wherein $R^4$ is nitro or nitroso
and Z is a leaving group which may be selected from halo, nitro and alkane-, arene- or alkylarenesulphonyloxy with a compound of formula (IV):

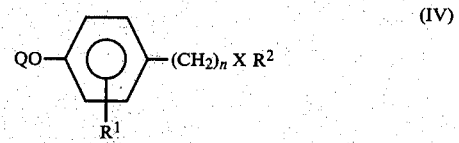

wherein Q is an alkali metal atom, an alkaline earth metal atom or the ammonium radical and n, X, $R^1$ and $R^2$ are as defined in formula (I). The reaction may conveniently be effected by standard methods known in the art which include reaction in an appropriate polar inert solvent at an expedient temperature.

Compounds of formula (I) wherein R is amino may also be prepared by the deprotection of the corresponding protected amino compounds, for example acylated compounds of formula (I) wherein R is mono- or dialkanoylamino of 1 to 4 carbon atoms (or comparable arylamino compounds such as benzamides) and $R^1$, $R^2$, n and X are as previously defined. The reaction can be effected by acid hydrolysis, for example, by refluxing with aqueous hydrochloric acid, and water or ethanol, by alkaline hydrolysis e.g. with ethanolic or aqueous sodium hydroxide solution. Protection of the amino group as arylidine derivatives (Schiff bases) allows especially ready removal of the arylidine group to produce the amine by using aqueous acid.

Suitable methods for the preparation of compounds of formula (I) wherein R is monoalkanoylamino or dialkanoylamino include the acylation of a compound of formula (I) wherein R is amino and $R^1$, $R^2$, n and X are as previously defined. The acylation may be effected by standard methods which include reaction with the appropriate acid anhydride or acid halide in a suitable inert polar solvent at an expedient temperature.

A compound of formula (I) may be used in the treatment of liver fluke infections in mammals including *F. hepatica* in ruminants including sheep, cattle, goat and buffalo, and in the pig and horse, and *F. gigantica* in ruminants including sheep and cattle. The compound is preferably administered orally at a dose between 10 and 250 mg/kg; and preferably between 30 and 150 mg/kg.

A compound of formula (I) may be administered for the treatment of liver fluke infections as the raw chemical, but preferably as an ingredient of a pharmaceutical formulation which contains in addition one or more inert carrier materials commonly used in pharmaceutical formulations as a vehicle for the active ingredient. The amount of active ingredient present in such formulations may vary according to one or more of several factors but may comprise from 0.0001% to 95% by weight of the formulation. The preferred formulations are those suitable for oral administration, containing from 5 to 95% by weight of a compound of formula (I). If presented as the raw chemical, then a compound of formula (I) is preferably in the form of a powder.

In the context of the present invention, the qualification 'inert' means that the carrier is pharmaceutically acceptable to the host of the infection to which the formulation is administered.

The presentation of an active ingredient (namely, a compound of formula (I)) in a pharmaceutical formulation may be as discrete units, such as tablets, capsules or cachets, each containing a predetermined amount of the active ingredient; as a powder or granules; or as a solution or a suspension in an aqueous liquid, a nonaqueous liquid, or a water-in-oil liquid emulsion. The active ingredient may also be presented as a bolus, electuary or paste; in the feed or a feed supplement intended for the host animal; in pellets, salt licks or block licks which are especially suitable for large animals such as sheep and cattle.

The formulations may be made by any of the methods of pharmacy but all methods include the step of bringing into association by admixture the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulations. The formulations contain one or more of the usual accessory ingredients used to prepare anthelmintic formulations including: solid and liquid diluents (for example, lactose, sucrose, glucose, starches, dicalcium phosphate or calcium phosphate for tablets, granules, dispersible and wettable powders, cachets and capsules; arachis oil, olive oil, or ethyl oleate for soft capsules; water, or vegetable oil for aqueous and non-aqueous suspensions, emulsions, and pastes); binders (for example, starch, sugar, glucose, methyl cellulose, gum acacia, Irish mosse or gelatin for granules and tablets); surface active agents (for example sodium lauryl sulphate, cetrimide or polyoxyethylene sorbitan monolaureate for tablets, powders and granules; sodium salt of an alkyl naphthalene sulphonic acid, sorbitan monooleate, ceto-stearyl alcohol and an emulsifier condensate of nonylphenol and ethylene oxide, for pastes and wettable powders); lubricating agents (for example liquid paraffin, talc, stearic acid, magnesium stearate or polyethylene glycol for tablets); dispersing agents (for example disodium salt of the condensation product of naphthalene sulphonic acid and formaldehyde, and calcium lignin sulphonate for wettable powders, pastes and suspensions); gelling agents (for example colloidal clays, sulphuric esters of a polysaccharide for aqueous suspension); suspending and thickening agents (for example gum tragacanth, xanthan gum, alginates, polyvinyl pyrrolidone, sodium carboxymethyl cellulose, and hydroxy-ethylcellulose for aqueous suspensions, aqueous-based pastes and wettable powders); and humectants (for example glycerine for water-based pastes); and other therapeutically acceptable accessory ingredients such as preservatives, buffers and antioxidants, which are known to be useful as carriers in such formulations.

A tablet may be prepared by compression or moulding, optionally with one or more accessory ingredients. Compressed tablets may be prepared by compressing in a suitable machine the active ingredient in a free flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Conveniently each tablet contains from 0.5 g. to 4.0 g of the active ingredient.

Granules may be made by the technique of wet granulation comprising moistening the powdered active ingredient with a binder in an inert liquid, and drying the moist mass; or by the techniques of precompression or slugging. The granules may be administered to animals in an inert liquid vehicle; or in a cachet or capsule of hard or soft gelatin preferably with liquid or powdered solid diluent; or in a suspension with a water or an oil base. In a drench or suspension, it is preferable to include further accessory ingredients such as a dispersing agent.

A dispersible or wettable powder may be made by admixing together the finely divided active ingredient with a wetting agent, and then administering the powder to the host animal as a suspension or dispersion in water. If desired a dispersing, suspending or thickening agent may be included. These formulations preferably contain from 15 to 85% by weight of the active ingredient.

A paste may be formulated in a liquid diluent which suspends the active ingredient. A stiffening or thickening agent may be included, together with a wetting agent and an humectant if the liquid diluent is water. If an emulsion paste is needed (oil-out or water-out), then one or more surface active agents should be included. From 25 to 80% by weight of these paste formulations may be comprised of the active ingredient but if the lower concentrations are used, then sufficient stiffening or thickening agent should be included to provide the desired viscosity.

Suspensions of the active ingredient in an inert liquid carrier are essentially the same as pastes but of a lower viscosity. They may be formulated using water or other inert diluent as the liquid carrier in association with a dispersing or wetting agent. Other ingredients such as thickening, gelling and suspending agents may also be included. These formulations may contain a wide range of concentrations of active ingredient, but of course, if too high a concentration is included the viscosity of the formulation will increase, and the formulations will become more of a paste than a suspension. Subject therefore to the concentration of the remaining ingredients, 5 to 50% by weight of the formulations may be comprised by the active ingredient.

In feed supplements, the active ingredient is generally present in large amounts relative to the accessory ingredients, and the supplements may be added directly or after intermediate blending or dilution. Examples of accessory ingredients for such formulations include solid orally ingestible carriers such as corn meal, attapulgite clay, soya flour, wheat shorts, soya grits, edible vegetable materials, and fermentation residues. The active ingredient is usually incorporated in one or more of the accessory ingredients and intimately and uniformly dispersed by grinding, tumbling or stirring with conventional apparatus. Formulations containing 1 to 90% by weight of the active ingredient are especially suitable for adding to feeds to provide a concentration desired to control infections by way of the animals' rations.

A compound of formula (I) may be administered either alone as the sole treatment for a liver fluke infection, or in combination with other substances which may complement or supplement its activity. Such additional substances may be administered simultaneously as a separate dose or in combination with a compound of formula (I) in a formulation, and may comprise other anthelmintics having activity against other parasites, such as cestodes (tapeworms) or nematodes. Such additional substances include phenothiazine; piperazine derivatives, for example the citrate, adipate or phosphate salts; organo-phosphorus compounds for example O,O-di-(2-chloroethyl)O-(3-chloro-4-methylcoumarin-7-yl)phosphate (Haloxon); 4-t-butyl-2-chlorophenyl N-methyl-O-methylphosphoramidate (Ruelene (Trade Name)); O,O-diethyl-O-(3-chloro-4-methyl-7-coumarinyl) phosphorothioate (Coumaphos); O,O-diethyl-O-naphthaloximide phosphate (Naphthalophos); O,O-dimethyl-2,2,2-trichloro-1-hydroxyethylphosphonate (Trichlorfon); benzimidazole anthelmintics including 2-(4-thiazolyl)benzimidazole (Thiabendazole); methyl 5-n-butybenzimidazole-2-carbamate (Parbendazole); and isopropyl-2-(4-thiazolyl)benzimidazole-5-carbamate (Cambendazole); quaternary ammonium anthelmintics including N-benzyl-N,N-dimethyl-N-(2-phenoxyethyl)ammonium salts such as the 3-hydroxy-2-naphthoate and embonate salts (Bephenium salts); N,N-dialkyl-4-alkoxy-α-naphthamidine anthelmintics including N,N-dibutyl-4-hexyloxy-α-naphthamidine (Bunamidine); salts of dl and 1-2,3,5,6-tetrahydro-6-phenylimidazo (2,1-b)thiazole (Tetramisole and Levamisole); trans-1-methyl-2-(2-(2-thienyl)vinyl)-1,4,5,6-tetrahydropyrimidine tartrate (Pyrantel tartrate); cis-1,4,5,6-tetrahydro-1-methyl-2-(2-(3-methyl-2-thienyl)vinyl)pyrimidine tartrate (Morantel tartrate); polyhalogenated benzanilide anthelmintics including 3,3',5,5',6-pentachloro-2,2'-dihydroxybenzanilide (Oxychlozanide); 2-acetoxy-4'-chloro-3,5-diiodobenzanilide (Clioxanide); 3,4',5-tribromosalicylanilide (Tribromsalan); 3,5-diiodo-3'-chloro-4'-(p-chlorophenoxy) salicylanilide (Rafoxanide); 4',5-dibromo-2-hydroxybenzanolide; 2,2'-dihydroxy-3,3'-dinitro-5,5'-dichlorobiphenyl (Menichlopholan); 2,2'-dihydroxy-3,3',5,5',6,6'-hexachlorodiphenylmethane (Hexachlorophene); 1,4-bis-(trichloromethyl)benzene (Hetol); 3-iodo-4-hydroxy-5-nitrobenzonitrile (Nitroxynil); and 5-chloro-N-(2'-chloro-4'-nitrophenyl)salicylamide (Niclosamide).

A particularly preferred combination comprises a compound of formula (I) and oxychlozanide, preferably in the ratio of 40 to 100 mg/kg and 2.5 to 15 mg/kg or lower respectively. Oxyclozanide is highly effective against adult liver flukes, and in combination with a compound of formula (I), complements its activity.

It will be appreciated that what we may claim may comprise any novel feature described herein but principally and not exclusively as follows:

(a) a compound of formula (I);

(b) a method of making such a compound of formula (I);

(c) a veterinary formulation comprising a compound of formula (I) together with a suitable carrier therefor;

(d) a method of making such a formulation and (d) a method for the treatment of liver fluke infections in a mammal comprising the administration of a compound or formulation as described in paragraphs (a) or (b) above.

The following examples illustrate aspects of this invention but in no way are to be construed as a limitation thereof.

EXAMPLE 1

Preparation of 4-(4-Acetamidophenoxy)-NN-dimethylbenzenesulphonamide

Chlorosulphonic acid (35 g) in dry carbon tetrachloride (50 ml) was cooled below 0° C. and a solution of 4-nitrodiphenyl ether (21.5 g) in dry carbon tetrachloride (50 ml) was added dropwise to the stirred mixture, the temperature being maintained at between −5° and 0° C. After 2 hours the solution was poured into ice-water with stirring, chloroform (200 ml) added, and the organic layer separated, washed with water and dried over anhydrous magnesium sulphate. Evaporation of the solvent gave a crystalline solid consisting of 4-(4-nitrophenoxy)benzenesulphonyl chloride.

The sulphonyl chloride (20.3 g) thus prepared was stirred with 25–30% w/v aqueous dimethylamine (200 ml) at 100° C. for 2 hours. One cooling, the solid was filtered off, washed with water and dried. Crystallisation from ethanol gave yellow needles of N,N-dimethyl-4-(4-nitrophenoxy)benzenesulphonamide, m.p. 116°–118° C.

Stannous chloride (34 g) was dissolved in concentrated hydrochloric acid (50 ml) and ethanol (50 ml). The solution was stirred at 100° C. and the foregoing sulphonamide (16 g) was added in small portions over 30 minutes. Stirring was continued for 2 hours after which the solution was cooled, poured into 5 N sodium hydroxide solution (200 ml) and stirred for 30 minutes. The resulting oil was extracted with ether. The residue, on removal of the ether, was dissolved in warm ethanol (60 ml) and acetic anhydride (15 ml) added to the cooled solution. On standing, crystals of 4-(4-acetamidophenoxy)-NN-dimethylbenzenesulphonamide, m.p. 174°–176° C. (ethanol), were obtained.

EXAMPLE 2

Preparation of 4-(4-Diacetylaminophenoxy)-NN-dimethylbenzenesulphonamide

The crude oily amine (12.6 g) obtained by stannous chloride reduction in Example 1 was heated for 2 hours at 100° C. with acetic anhydride, cooled and diluted with ether (400 ml), whereupon crystals were obtained of 4-(4-diacetylaminophenoxy)-NN-dimethylbenzenesulphonamide, m.p. 175°–178° C. (from ethanol).

EXAMPLE 3

Preparation of 4-(4-Aminophenoxy)-NN-dimethylbenzenesulphonamide hydrochloride 4-(4-Acetamidophenoxy)-NN-dimethylbenzenesulphonamide (Example 1) was refluxed with 2 N aqueous hydrochloric acid (25 ml) and ethanol (25 ml) for 2 hours. Evaporation to dryness gave a residue of 4-(4-aminophenoxy)-NN-dimethylbenzenesulphonamide hydrochloride, which formed crystals, m.p. 196°–198° C., from benzene-ethanol.

EXAMPLE 4

Preparation of 4-(4-Aminophenoxy)-N-cyclohexylbenzenesulphonamide 4-(4-Nitrophenoxy)benzenesulphonyl chloride (Example 1) (18.8 g), cyclohexylamine (6.5 g), anhydrous potassium carbonate (8.3 g) and acetone (100 ml) were refluxed together for 4 hours. On concentration and addition of water, an oil separated which solidified overnight. From ethanol on addition of light petroleum (b.p. 60°–80° C.), 4-(4-nitrophenoxy)-N-cyclohexylbenzenesulphonamide was obtained in the form of crystals, m.p. 94° C.

The reduction followed the method of Example from the nitro-compound (12.5 g) 4-(4-aminophenoxy)-N-cyclohexylbenzenesulphonamide was obtained as a solid which, from ethanol-light petroleum (b.p. 60°–80° C.) gave crystals m.p. 133°–135° C. containing 0.5% water of crystallisation.

EXAMPLE 5

Preparation of 4-(4-Aminophenoxy)-N-methylbenzenesulphonamide

From 4-p-Nitrophenoxybenzenesulphonyl chloride (20 g) and 40% aqueous methylamine (200 ml) heated together at 100° C. for 2 hours, was obtained 4-(4-nitrophenoxy-N-methylbenzenesulphonamide which gave crystals m.p. 139°–140° C. from ethanol.

The nitro-compound (3.1 g) suspended in acetic acid (10.8 g) with addition of water (14 ml) was stirred at 70°–75° C., while powdered iron (3.55 g) was added in portions over 30 minutes. After further stirring (30 minutes) the iron sludge was filtered off and the solution diluted with water to give 4-(4-aminophenoxy)-N-methylbenzenesulphonamide as an oil which slowly solidified. From ethanol the base formed crystals, m.p. 121°–122° C.

EXAMPLES 6 to 10

In accordance with the method described in Example 5 there were prepared the following:

EXAMPLE 6

4-(4-aminophenoxy)-N-ethylbenzenesulphonamide, m.p. 109°–110° C.

EXAMPLE 7

4-(4-aminophenoxy)-N-n-propylbenzenesulphonamide, m.p. 114°–116° C.

EXAMPLE 8

4-(4-aminophenoxy)-N-i-propylbenzenesulphonamide, m.p. 139°–141°C.

EXAMPLE 9

4-(4-aminophenoxy)-N-n-butylbenzenesulphonamide, m.p. 150°–152° C.

EXAMPLE 10

4-(4-aminophenoxy)-N-i-butylbenzenesulphonamide, m.p. 122°–124° C.

EXAMPLE 11

Preparation of 4-(4-Acetamidophenoxy)-N-methylbenzenesulphonamide

The amine prepared in Example 5 (8 g) was acetylated by allowing its solution in ethanol (80 ml) containing acetic anhydride (16 ml) to stand at room temperature. The precipitated 4-(4-acetamidophenoxy)-N-methylbenzenesulphonamide, after recrystallisation from ethanol, had m.p. 183°–184° C.

EXAMPLES 12 to 15

In accordance with the method described in Example 11, there were prepared the following:

EXAMPLE 12

4-(4-acetamidophenoxy)-N-ethylbenzenesulphonamide, m.p. 156°–158° C.

EXAMPLE 13

4-(4-acetamidophenoxy)-N-n-propylbenzenesulphonamide, m.p. 148°–149° C.

EXAMPLE 14

4-(4-acetamidophenoxy)-N-i-propylbenzenesulphonamide, m.p. 159°–162° C.

EXAMPLE 15

4-(4-acetamidophenoxy)-N-n-butylbenzenesulphonamide, m.p. 138°–141° C.

EXAMPLE 16

Aqueous Suspensions

| | | | | | |
|---|---|---|---|---|---|
| Compound of Ex. 1 | 5.0% | 20.00% | 40.00% | 50.00% | w/w |
| Bentonite (Gelling Agent) | 2.5% | 1.50% | 1.00% | 1.00% | w/w |
| Bevaloid Dispersant (Trade Mark) (Dispersing agent) | 1.0% | 1.00% | 1.00% | 1.00% | w/w |
| Sodium Benzoate (Buffering agent) | 1.0% | 1.00% | 1.00% | 1.00% | w/w |
| Water | 90.5% | 76.50% | 57.00% | 47.00% | w/w |

-continued

|  |  |  |  |
|---|---|---|---|
| 100.0% | 100.00% | 100.00% | 100.00% w/w |

The bentonite was dispersed in some of the water, the Bevaloid Dispersant and sodium benzoate added, and finally the finely ground active ingredient with the water. The whole was mixed until uniform.

Bentonite is a colloidal clay consisting principally of montmorilonite and Bevaloid Dispersant is a disodium salt of the condensation product of naphthalene sulphonic acid and formaldehyde.

| Compound of Ex. 1 | 30.00% w/w | 20.00% w/w | 50.00% w/w |
|---|---|---|---|
| Sulphite Residue (Dispersing agent) | 5.00% w/w | 5.00% | 5.00% w/w |
| Carmoss (Gelling agent) (Trade Mark) | 0.75% w/w | 0.75% w/w | 0.75% w/w |
| Water | 64.25% w/w | 74.25% w/w | 44.25% w/w |
|  | 100.00 w/w | 100.00% w/w | 100.00% w/w |

The Carmoss and sulphite residue were dissolved in the water, the finely ground active ingredient added, and the whole mixed until uniform.

Sulphite residue is crude calcium lignin sulphonate; Carmoss is a carragenate or a sulphuric acid ester of a polysaccharide.

EXAMPLE 18

Aqueous Suspension

| Compound of Ex. 11 | 5.0% w/w |
|---|---|
| Neosyl (Trade Mark) (Diluent) | 5.0% w/w |
| Carmoss (Gelling agent) (Trade Mark) | 1.5% w/w |
| Bevaloid Dispersant (Trade Mark) (Dispersing agent) | 1.0% w/w |
| Water | 87.5% w/w |
|  | 100.0% w/w |

The Carmoss and Bevaloid Dispersant were mixed with the water, and then the finely ground active ingredient was then added and the whole mixed until uniform. Where China clay was an ingredient, it was included at the same time as the addition of Bentone 38 is a cationic substituted with a quaternary ammonium base.

EXAMPLE 19

Water-based Pastes

| Compound of Ex. 11 | 23.0% | 55.00% | 60.00% | 45.00% w/w |
|---|---|---|---|---|
| Keltrol (Trade Mark) (Suspending agent) | 0.5% | 0.50% | 0.45% | 0.55% w/w |
| Neosyl (Trade Mark) (Diluent) | 18.3% | — | 5.00% | — w/w |
| Glycerine (Humectant) | 23.0% | 20.00% | 18.00% | 32.00% w/w |
| Water | 35.2% | 24.50% | 16.55% | 32.45% w/w |
|  | 100.0% | 100.00% | 100.00% | 100.00% w/w |

The Keltrol was dissolved in the water, the remaining ingredients incorporated, and the whole mixed until uniform.

Keltrol is a xanthan gum, a high molecular weight linear polysaccharide.

EXAMPLE 20

Water-based Pastes

| Compound of Ex. 11 | 20.0% | 50.00% | 60.00% | 40.00% w/w |
|---|---|---|---|---|
| Bevaloid Dispersant (Trade Mark) (Dispersing agent) | 0.5% | 0.50% | 0.40% | 0.60% w/w |
| Gum tragacanth (Suspending agent) | 3.5% | 2.00% | 1.60% | 2.40% w/w |
| Glycerine (Humectant) | 16.0% | 8.50% | 8.00% | 11.00% w/w |
| Water | 60.0% | 39.00% | 30.00% | 46.00% w/w |
|  | 100.0% | 100.00% | 100.00% | 100.00% w/w |

The gum tragacanth was dissolved in the mixture of water and glycerine, and the finely divided active ingredient incorporated to provide a uniform paste.

EXAMPLE 21

Pastes

| Compound of Ex. 10 | 50.0% | 60.0% | 50.0% | 60.0% | 20.0% w/w |
|---|---|---|---|---|---|
| Polyethylene Glycol 400 | 40.0% | 32.0% | 50.0% | 40.0% | 45.0% w/w |
| Polyethylene Glycol 4000 | 10.0% | 8.0% | — | — | 5.0% w/w |
| China clay (Solid diluent) | — | — | — | — | 30.0% w/w |
|  | 100.0% | 100.0% | 100.0% | 100.0% | 100.0% w/w |

Both glycols, or the single glycol, as appropriate, were heated together, and when uniform, the finely ground active ingredient (together with the china clay, if appropriate) was added, and the mixture stirred to provide a paste of uniform consistency.

EXAMPLE 22

Pastes

| Compound of Ex. 10 | 50.0% | 60.0% | 40.0% | 20.0% w/w |
|---|---|---|---|---|
| Carmoss (Trade Mark) (Thickening agent) | 2.0% | 1.6% | 2.5% | 1.7% w/w |
| Glycerine (Humectant) | 10.0% | 8.0% | 12.0% | 8.3% w/w |
| Water | 38.0% | 30.4% | 45.4% | 31.7% w/w |
| China clay (Solid Diluent) | — | — | — | 38.3% w/w |
|  | 100.0% | 100.0% | 100.0 | 100.0% w/w |

The Carmoss was dissolved in the water, the glycerine added, followed by the active ingredient (and China Clay, if appropriate). The whole was mixed until uniform.

Carmoss is a carragenate or a sulphuric acid ester of a polysaccharide.

EXAMPLE 23

Pastes

| Compound of Ex. 10 | 60.0% | 70.00% | 45.0% | 20.0% w/w |
|---|---|---|---|---|
| Manucol (Trade Mark) (Thickening agent) | 0.3% | 0.25% | 0.4% | 1.5% w/w |
| Glycerine (Humectant) | 8.0% | 6.00% | 11.0% | 5.0% w/w |
| Water | 31.7% | 23.75% | 43.6% | 38.5% w/w |
| China clay (Solid Diluent) | — | — | — | — |
| | 100.0% | 100.00% | 100.0% | 100.0% w/w |

The Manucol was dissolved in the water and glycerine and the active ingredient (and China Clay, if appropriate) added and mixed until uniform.

Manucol is sodium alginate.

EXAMPLE 24

Oil-in-Water Emulsion Pastes

| Compound of Ex. 5 | 5.00% w/w | 50.0% w/w |
|---|---|---|
| Sipol Wax AO (Trade Mark) (Emulsifying agent) | 6.25% w/w | 5.0% w/w |
| Mineral Oil (Liquid Diluent) | 25.00% w/w | 20.0% w/w |
| Water | 31.35% w/w | 25.0% w/w |
| China Clay (Solid Diluent) | 17.50% w/w | — |
| | 100.00% w/w | 100.0% w/w |

The Sipol wax AO was dissolved in the mineral oil at 60° C., and this solution then added with vigorous stirring to the water, also at 60° C. Stirring was continued until the emulsion was cooled to 25°–30° C., at which temperature the finely ground active ingredient (and the China Clay where appropriate) was added, and the whole mixed until uniform.

Sipol wax AO is Cetomacrogol Emulsifying Wax BPC.

EXAMPLE 25

Wettable Powders

| Compound of Ex. 5 | 85.0% w/w | 20.0% w/w |
|---|---|---|
| Neosyl (Trade Mark) (Diluent) | 1.0% w/w | 24.0% w/w |
| Bevaloid Dispersant (Trade Mark) (Dispersing agent) | 2.0% w/w | 2.0% w/w |
| Perminal BX (Trade Mark) (Wetting agent) | 0.2% w/w | 0.2% w/w |
| Natrosol 250 (Trade Mark) (Suspending agent) | 1.7% w/w | 2.8% w/w |
| Sodium sulphate (Suspending agent) | 10.1% w/w | 51.0% w/w |
| | 100.0% w/w | 100.0% w/w |

The raw materials were mixed together to provide a powder of uniform consistency. Perminal BX is the sodium salt of alkylated naphthalene sulphonic acid.

EXAMPLE 26

Feed Premixes

| Compound of Ex. 5 | 1% w/w | 80% w/w |
|---|---|---|
| Cereal Base | 99% w/w | 20% w/w |

The two materials were mixed to provide a premix of uniform consistency.

EXAMPLE 27

Pellets

| Compound of Ex. 12 | 1% w/w | 80% w/w |
|---|---|---|
| Cereal Base | 99% w/w | 20% w/w |

The two ingredients were mixed, and the mixture then fed to any conventional feedstuff pelleting plant.

EXAMPLE 28

Tablets

Tablets were prepared from the following ingredients:

| | per tablet |
|---|---|
| Compound of Ex. 12 | 2000 mg |
| Starch B.P. | 300 mg |
| Povidone B.P.C. | 50 mg |
| Magnesium stearate B.P. | 25 mg | and half the quantity of starch were granulated with a solution of povidone in 50% aqueous ethanol, and dried. The remainder of starch and Magnesium stearate were added and the whole mixed. The resulting granules were then compressed with a suitably shaped punch.

EXAMPLE 29

Tablets

Tablets were prepared from the following ingredients:

| | per tablet |
|---|---|
| Compound of Ex. 12 | 2000 mg |
| Microcrystalline cellulose | 1000 mg |
| Methylhydroxyethylcellulose | 50 mg |
| Starch B.P. | 250 mg |
| Magnesium stearate. | 30 mg |

Item 1, together with half the quantity of items 2 and 4, were granulated with a solution of item 3 in 50% aqueous ethanol, and then dried. The remainder of items 2 and 4 were added, and then item 5, and the whole mixed together. The resulting granules were dried and then compressed to form tablets.

EXAMPLE 30

Groups of five mice were each injected at day zero with 12 *Fasciola gigantica* metacercariae.

The mice in each group were orally dosed with a compound of formula (I) once on days 6 to 10 inclusive— At day 31 the mice were autopsied to ascertain the number of living metacercariae in the liver.

The percentage inhibition of the treated groups of mice was termined for each compound tested by comparison with undosed controlled groups similarly infected at day zero with 12 *F. gigantica* metacercariae and autopsied at day 31.

The results are illustrated in Table 1 where the following score has been used to indicate percentage inhibition.

| SCORE | INHIBITION |
|---|---|
| ++++ | (91-100)% |
| +++ | (75-90)% |
| ++ | (51.74)% |

Percentage inhibition =
$\frac{\text{Number of living metacercariae in treated group}}{\text{number of living metacerariae in control group}} \times 100\%$

TABLE 1

% inhibition of *F. gigantica* metacerariae in mice treated with certain compounds of formula (1)

| COMPOUND | DOSE mg/kg orally | SCORE |
|---|---|---|
| 4-(4-Acetamidophenoxy)phenyl-NN-dimethyl sulphone | 200 | ++++ |
| 4-(4-Acetamidophenoxy)phenyl-N-methyl sulphone | 200 | ++++ |
| 4-(4-Aminophenoxy)phenyl-N-methyl sulphone | 200 | ++++ |
| 4-(4-Acetamidophenoxy)phenyl-N-ethyl sulphone | 200 | ++++ |
| 4-(4-Acetamidophenoxy)phenyl-N-i-propyl sulphone | 200 | ++++ |
| 4-(4-Aminophenoxy)phenyl-N-i-propyl sulphone | 200 | ++++ |
| 4-(4-Aminophenoxy)phenyl-N-n-butyl sulphone | 200 | ++++ |
| 4-(4-Aminophenoxy)phenyl-N-i-butyl sulphone | 200 | ++++ |

What we claim is:

1. A method for the treatment of a liver fluke infection in a mammal comprising the administration to said mammal of an anti-liver-fluke infection effective amount of a diphenylether of the formula

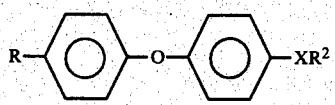

or an acid addition salt thereof wherein R is selected from amino, monoalkanoylamino and dialkanoylamino, both of one to four carbon atoms;

$R^2$ is $NR^8R^9$ wherein $R^8$ is selected from alkyl of one to four carbon atoms, hydroxyalkyl of one to four carbon atoms, aryl of six to ten carbon atoms and cycloalkyl of three to eight carbon atoms, and $R^9$ is selected from $R^8$ as defined and hydrogen; and X is S, SO or $SO_2$.

2. The method of claim 1 in which the diphenylether is 4-(4-Acetamidophenoxy)-N,N-dimethylbenzenesulphonamide or an acid addition salt thereof.

3. The method of claim 1 in which the diphenylether is 4-(4-Diacetylaminophenoxy)-N,N-dimethylbenzenesulphonamide or an acid addition salt thereof.

4. The method of claim 1 in which the diphenylether is 4-(4-Aminophenoxy)-N,N-dimethylbenzenesulphonamide or an acid addition salt thereof.

5. The method of claim 1 in which the diphenylether is 4-(4-Aminophenoxy)-N-cyclohexylbenzenesulphonamide or an acid addition salt thereof.

6. The method of claim 1 in which the diphenylether is 4-(4-Aminophenoxy)-N-methylbenzenesulphonamide or an acid addition salt thereof.

7. The method of claim 1 in which the diphenylether is 4-(4-Aminophenoxy)-N-ethylbenzenesulphonamide or an acid addition salt thereof.

8. The method of claim 1 in which the diphenylether is 4-(4-Aminophenoxy)-N-n-propylbenzenesulphonamide or an acid addition salt thereof.

9. The method of claim 1 in which the diphenylether is 4-(4-Aminophenoxy)-N-i-propylbenzenesulphonamide or an acid addition salt thereof.

10. The method of claim 1 in which the diphenylether is 4-(4-Aminophenoxy)-N-n-butylbenzenesulphonamide or an acid addition salt thereof.

11. The method of claim 1 in which the diphenylether is 4-(4-Aminophenoxy)-N-i-butylbenzenesulphonamide or an acid addition salt thereof.

12. The method of claim 1 in which the diphenylether is 4-(4-Acetamidophenoxy)-N-methylbenzenesulphonamide or an acid addition salt thereof.

13. The method of claim 1 in which the diphenylether is 4-(4-Acetamidophenoxy)-N-ethylbenzenesulphonamide or an acid addition salt thereof.

14. The method of claim 1 in which the diphenylether is 4-(4-Acetamidophenoxy)-N-n-propylbenzenesulphonamide or an acid addition salt thereof.

15. The method of claim 1 in which the diphenylether is 4-(4-Acetamidophenoxy)-N-i-propylbenzenesulphonamide or an acid addition salt thereof.

16. The method of claim 1 in which the diphenylether is 4-(4-Acetamidophenoxy)-N-n-butylbenzenesulphonamide or an acid addition salt thereof.

17. The method of claim 1 in which the compound or salt is administered in association with a veterinarily acceptable carrier therefor.

* * * * *